Figure 1:
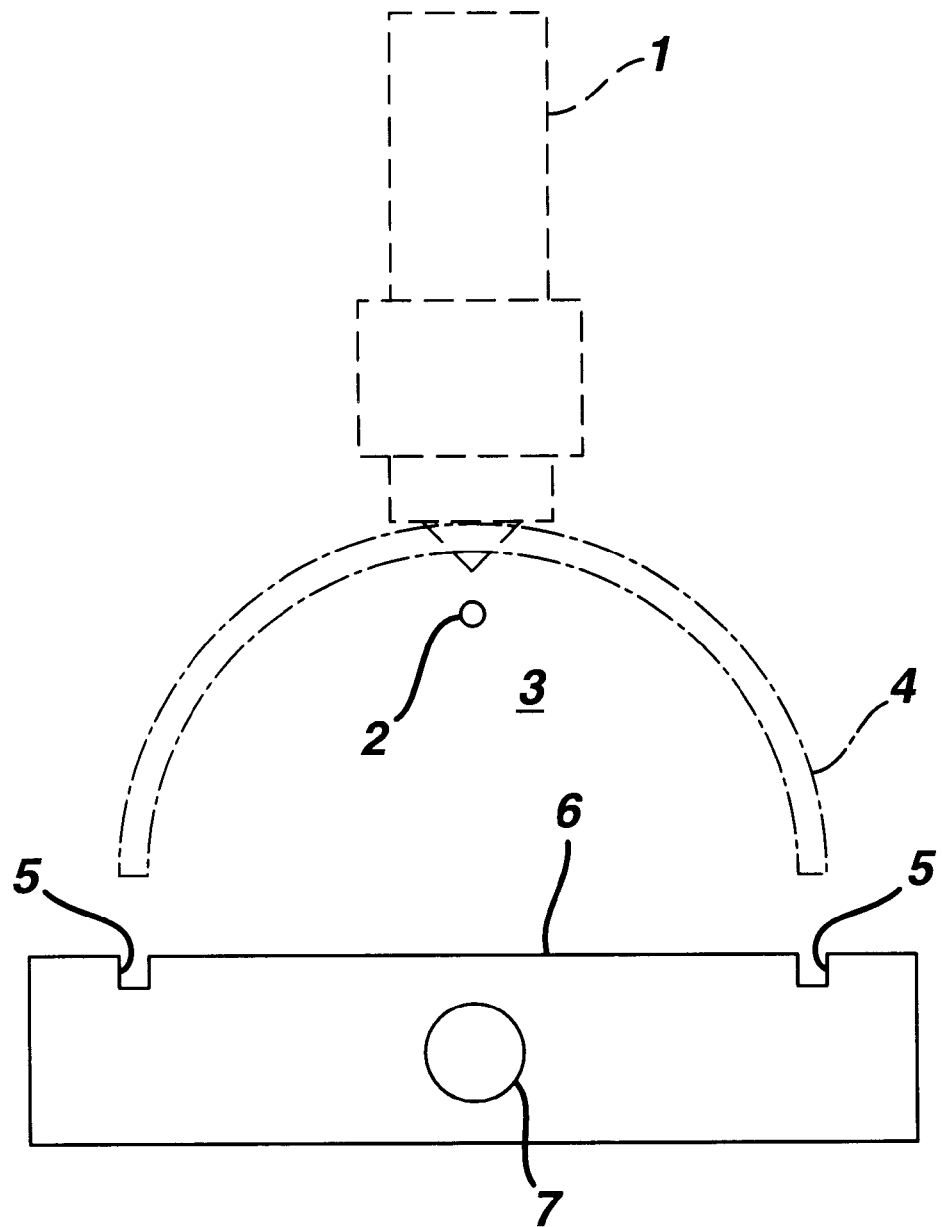

United States Patent [19]

Desai

[11] Patent Number: 6,146,687
[45] Date of Patent: Nov. 14, 2000

[54] METHOD OF COATING A FIBER

[75] Inventor: Pranav Desai, Anaheim Hills, Calif.

[73] Assignee: Gillette Canada Inc., Kirkland, Canada

[21] Appl. No.: 09/198,905

[22] Filed: Nov. 24, 1998

[51] Int. Cl.[7] .................................. B05D 1/02; B05D 3/00
[52] U.S. Cl. ........................ 427/2.29; 424/443; 424/502; 427/2.31; 427/345
[58] Field of Search ................ 427/2.29, 2.31, 427/2.15, 2.14, 345; 132/321; 424/401, 443, 502

[56] References Cited

U.S. PATENT DOCUMENTS

| | | | |
|---|---|---|---|
| 3,943,949 | 3/1976 | Ashton et al. | 132/89 |
| 4,033,365 | 7/1977 | Klepak et al. | 132/89 |
| 4,414,990 | 11/1983 | Yost | 132/91 |
| 4,532,929 | 8/1985 | Mattei et al. | 427/2.31 |
| 4,568,560 | 2/1986 | Schobel | 427/3 |
| 4,777,046 | 10/1988 | Iwakura et al. | 424/435 |
| 4,911,927 | 3/1990 | Hill et al. | 424/443 |
| 5,000,980 | 3/1991 | Berger | 427/180 |
| 5,061,510 | 10/1991 | Nussbaumer et al. | 427/180 |
| 5,073,365 | 12/1991 | Katz et al. | 427/2.31 |
| 5,209,251 | 5/1993 | Curtis et al. | 132/321 |
| 5,329,881 | 7/1994 | O'Rourke | 427/2.29 |
| 5,433,960 | 7/1995 | Meyers | 426/5 |
| 5,680,876 | 10/1997 | Hasham et al. | 132/329 |
| 5,819,768 | 10/1998 | Bible et al. | 132/321 |
| 5,918,609 | 7/1999 | Tsao et al. | 132/321 |
| 5,937,874 | 8/1999 | Guay et al. | 132/321 |

*Primary Examiner*—Diana Dudash
*Assistant Examiner*—Bret Chen
*Attorney, Agent, or Firm*—David A. Howley

[57] ABSTRACT

A method and apparatus for coating a fiber used in oral hygiene. The method comprises aerosolizing a coating and projecting the aerosolized coating particles onto a target area of the fiber. The method also comprises recycling recaptured coating particles for reuse in fiber coating. An apparatus for coating oral hygiene fibers is also described.

11 Claims, 1 Drawing Sheet

METHOD OF COATING A FIBER

BACKGROUND OF THE INVENTION

1. Field of the Invention

This invention relates generally to the field of manufacturing coated fibers. More specifically, the invention relates to methods and apparatus for coating of fibers used in oral hygiene.

2. Description of Related Art

Tooth decay and dental disease can be caused by bacterial action resulting from the formation of plaque about the teeth and/or the entrapment of food particles in interstices between the teeth. Removal of plaque and entrapped food particles reduces the incidence of caries, gingivitis, and mouth odors as well as generally improving oral hygiene. Conventional brushing has been found to be inadequate for removing all entrapped food particles and plaque. To supplement brushing, dental flosses and tapes have been recommended.

Dental flosses with a formulation of a waxed coating applied to the dental thread have been found to be easier to insert between adjacent teeth than unwaxed floss due to the reduced friction of the waxed fiber against tooth enamel. Additives to color or flavor the floss, or to enhance the floss's ability to fight tooth decay can be added to the wax formulation before application to the floss, with the wax acting as a carrier for the additives.

Conventionally, wax has been applied to the floss by direct contact with hot, molten wax, either by dragging the floss through a molten bath of wax or across a rotating surface covered in molten wax. In the latter designated "roller method," molten wax is delivered to the rotating cylinder by submerging a lower portion of the roller in a molten bath of wax containing the coating formulation. The coating is transferred to the floss as it moves in contact across the top of the roller. The roller method of manufacturing coated fibers has certain disadvantages.

A primary disadvantage is that the roller method exposes the coating formulation to the atmosphere for prolonged periods of time resulting in increased oxidation of the formulation. The oxidation of the formulation before application decreases its subsequent chemical stability resulting in a diminished shelf-life of the final dental product. Also, oxidation of the formulation results in an undesirable appearance to the coating leading to consumer avoidance of the product. To avoid these difficulties, the formulation is frequently discarded and replaced during the manufacturing process. However, frequent replenishment results in increased waste and manufacturing expense. The roller method also results in an inconsistent application level along the length of a the fiber resulting in uneven coating levels.

Additionally, to keep the roller formulation flowable, it must remain heated throughout the application process. Heating increases the rate of oxidation and drives up manufacturing costs through increased energy expenditure. Heating also prevents ease of handling the formulation with heated formulation frequently splashing on to manufacturing equipment thereby increasing capital depreciation and maintenance costs. Additionally, heating increases the rate of evaporation of volatile additives, such as flavor oils, that are added to the coating formulation. Loss of these additives also increases manufacturing costs and leads to unwanted deviations from the chemical composition of the coating formulation. Heating and exposure of the formulation also pollute the manufacturing plant, requiring extraction of the volatilized fumes to prevent worker exposure to their potentially noxious effects.

Finally, the roller method is a 'wet' process that is detrimental to a characteristic of the dental product—i.e., fiber bulking that is desirable. The application of 'wet' coatings with the subsequent required drying process required (due to the heavy weight of the 'wet' formulation) decreases to desired bulking property characteristics.

The present invention provides the advantage of a manufacturing method and apparatus; (1) that minimizes the oxidation and volatilization of fiber coating formulation and ingredients, (2) that decreases energy and manufacturing costs, (3) that increases safety for plant workers and (4) that preserves desired characteristics of the oral hygiene product fiber.

SUMMARY OF THE INVENTION

The present invention provides a method and apparatus for manufacturing coated fibers used in oral hygiene. The method comprises the step of aerosolization, at ambient temperature, of a coating formulation onto a target area of a fiber. The apparatus comprises an enclosed device in which a coating formulation is aerosolized and overspray aerosolized particles are recycled.

An advantage of the invention is the elimination of the heating of fiber coating formulations and minimizing of exposure of the formulation to the surrounding air.

Another advantage of the invention is to improve the stability of the applied coating by eliminating oxidation of the formulation before application to the fiber.

It is another advantage to provide consistent levels of coating formulation over the entire length of the fiber. It is another advantage of the invention to prevent de-bulking of the coated fiber by eliminating 'wet' fiber application. It is another advantage of the invention to eliminate the need for drying the 'wetted fiber' thereby further reducing the manufacturing costs.

A further advantage of aerosolization is that application by aerosol permits deeper penetration of the formulation into and throughout the flossy (baulking) section of the fiber.

BRIEF DESCRIPTION OF THE DRAWING

FIGURE is a view of an apparatus for applying aerosolized formulation to a fiber.

DETAILED DESCRIPTION OF THE PREFERRED EMBODIMENTS

It is to be understood that the terminology used herein is for the purpose of describing particular embodiments, and is not intended to limit the scope of the present invention, which will be limited only by the appended claims.

It must be noted that as used herein and in the appended claims, the singular forms "a," "an," and "the" include plural referents unless the context clearly dictates otherwise. Thus, for example, reference to "a formulation" includes mixtures of different formulations, reference to "an inert material" includes one or more of such materials, and reference to "the method of coating" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited.

All publications discussed herein are provided solely for their disclosure prior to the filing date of the present application. Nothing herein is to be construed as an admission that the inventors are not entitled to antedate such disclosure by virtue of prior invention. The term "fiber," as used herein, includes dental flosses, dental tapes, and similar articles used for oral hygiene comprising any natural or traditional yarn such as cotton or any synthetic fiber such as polyamide, polyester, UHM-PE (ultra high molecular weight polyethylene), THV (by 3M™), PVDF (polyvinylidene fluoride) or any combination thereof. The term also includes any braided fiber that is made of a braided shell and a soft core. The term "braiding or braided shell" includes using any natural, synthetic manmade fibers, or combination of such fibers (such as polyamide, polyester, PTFE, etc.) with different numbers of ends and number of picks, braided on a soft core. The term "soft core" includes any elastic monofilament, foam, or microtube which can also be an effective delivery system to provide cosmetic, therapeutic or clinical agents for use in oral hygiene.

The terms "aerosol," "aerosolized particles" and "aerosolized particles of a coating formulation" shall mean particles of a formulation that comprise a wax, a medicament, a sealant, an emulsion, an abrasive, an adhesive, a friction reducer, an encapsulated composition, an additive, a flavor, a pharmaceutical composition, or any combination thereof, that are formed upon forcing a formulation through an opening in a nozzle. The aerosol particles have a size which is sufficiently small such that when the particles are formed they remain suspended in the air for a sufficient amount of time such that a fiber incorporates the particles into the warp and weave and/or onto the surface of the fiber. The total preferred volume of aerosol supplied to a target area of fiber is in the range of about one foot in length is in the range of about 50 ml and less than 1 liter. The particles of the aerosolized formulation typically have a diameter in the range of about 5 to 500 microns.

The method for generating the aerosol comprises passing the formulation through a small nozzle aperture in the range of about 0.25 mm to 1.0 mm in diameter under force. The force can be supplied by pressure, electric field, electromagnetism, or gravity. In a preferred embodiment the forces is supplied by air pressure. The preferred pressure being in the range of about 10–25 psi and more preferably in the range of about 5–7 psi. "Ambient temperature" is room temperature, typically in the range of about 18–20° C. The term "nozzle" means any sprout, mouthpiece or end fitted to a hose or communicating container with an opening designed to eject a formulation in aerosolized form. The nozzle is preferably in the shape of a circle with a diameter in the range of 0.01 to 0.02 inch. An exemplary nozzle is 0.0128 inches in diameter. The particles have a size which is sufficiently small such that when the particles are formed they remain suspended in the air for a sufficient amount of time such that the target area of the fiber can be sufficiently impregnated or coated with the formulation.

By the term "formulation" and "coating formulation" is meant, a flowable composition that forms an aerosol upon passage through the aperture of a nozzle. Formulations of the present invention comprise waxes, medicaments, sealants, emulsions, abrasives, adhesives, friction reducers, encapsulated compositions, additives, flavors, pharmaceutically active compositions, or any combination or mixtures thereof. The terms "combination" or "mixtures" as used in relation to the "formulations" and "coating formulations" described herein, include multiple applications of any of the "formulations" and "coating formulations," such that a first coating of the fiber is followed by a second coating using a different formulation so that the final fiber can have a multiple number of coatings of any of the formulations described herein. Alternatively, a single coating of a mixture of any number of members of the group making up a formulation can be applied to the fiber during one "coating event." Any single or multiple applications of an aerosol of a fiber resulting in a mixture or combination of the formulations described herein are contemplated by the methods of the invention.

The term "coating event" shall be interpreted to mean the administration of a coating formulation to a fiber of 100 meter length for a time sufficient to impregnate the fiber thoroughly from a dispensing device over a period of time of 60 seconds or less, preferably 40 seconds or less, and more preferably 38 seconds or less. A typical coating event shall involve the administration of a coating formulation to a fiber in an amount of about 30.33 grams/100 m. to about 35 grams/100 m. which involves the release of from about 38.73 grams to about 40 grams of coating formulation from the apparatus. In that a composition of the coating formulation is dissolved in a carrier to form the formulation the amount of pharmaceutical delivered maybe very small and will vary with the concentration of pharmaceutical in the carrier. Such formulations include, aqueous solutions, ethanoic solutions, aqueous/ethanoic solutions, saline solutions, colloidal suspensions and microcrystalline suspensions. In a preferred embodiment the formulation is a flowable wax.

The term "medicaments" or "pharmaceutically active compositions" described herein comprise: anti-caries agents, fluorides, or pharmaceuticals effective in the treatment, amelioration or modification of gum, tooth or mouth disease. The "additives" described herein include volatile compounds comprising flavorings suitable for human consumption. The pharmaceutical compositions described herein also comprise a pharmaceutically active drug and any pharmaceutically acceptable carrier (e.g., water and/or ethanol) effective in the treatment, amelioration or modification of gum, tooth or mouth disease. Such formulations include, aqueous solutions, ethanoic solutions, aqueous/ethanoic solutions, saline solutions, colloidal suspensions and microcrystalline suspensions. Preferred coating formulations are comprised of a wax, a medicament, a sealant, an emulsion, an abrasive, an adhesive, a friction reducer, an encapsulated composition, an additive, a flavor or any combination or mixture thereof. Pharmaceutically acceptable carrier preparations include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate.

Aqueous carriers include water, alcoholic/aqueous solutions, emulsions or suspensions, including saline and buffered media. The active pharmaceutical ingredient is often mixed with excipients that are pharmaceutically acceptable and compatible with the active ingredient. Suitable excipients include water, saline, dextrose, glycerol and ethanol, or combinations thereof. Preservatives and other additives may also be present in the formulation such as, for example, antimicrobial, antioxidants, chelating agents, and the like.

The term "carrier" shall mean a liquid, flowable, pharmaceutically acceptable excipient material in which a coating formulation is suspended in or, more preferably, dissolved in. Useful carriers do not adversely interact with the coating formulation and have properties that allow for the formation of aerosolized particles of the coating formulation as previously described. Preferred carriers include water, ethanol, saline solutions and mixtures thereof with pure water being preferred. Other carriers can be used provided that they can be formulated to create a suitable aerosol and do not adversely affect the coating formulation or the target fiber.

"Therapeutically effective" as used herein, refers to an amount of formulation or composition or reagent in a pharmaceutical acceptable carrier that is of sufficient quantity to ameliorate the state of the patient so treated. "Ameliorate" refers to a lessening of the detrimental effect of the disease state or disorder of an oral, gum, or tooth disease. The term "modulate" means inhibit, alter, or decrease the expression or progression of an oral, gum or tooth disease.

The "reservoir" or "storage container" and the "collecting surface" of the apparatus of the present invention are preferably comprised of inert materials. The formulations may be stored in the reservoir or storage container for extended periods of time without the formulation contained therein appreciable changing due to any activity, reactivity, or effect due to contact with the container or with the outside atmosphere. By the term "inert" is meant, a substance lacking any activity, reactivity, or effect. The term inert is particularly relevant with respect to a formulation contained inside a reservoir or storage container comprised of inert material. Interconnecting means that include one or more open or closed channels, also comprised of inert material, that provide fluid communication between a collecting surface, a first reservoir or storage container and any additional containers are also encompassed by the apparatus of the invention. The term "collecting surface" shall mean a surface on the inside of the apparatus upon which the aerosolized "overspray" is deposited. By "overspray" is meant any aerosolized formulation that is not deposited or coated on or within a fiber. The overspray is collected after deposition on an inside surface of the apparatus of the invention termed the "collecting surface." Additionally, the collecting surface of the apparatus is in heating communication with a heating means that raises the temperature of the collecting surface in the range of about 22° C. to about 27° C. thereby causing the formulation to achieve flowability so that it drains under the force of gravity into a channel in fluid communication with a reservoir or storage container of the apparatus.

The apparatus of the invention for delivery of an aerosolized coating formulation to a target area of a fiber also comprises secondary or additional containers or reservoirs preferably also containing a formulation, also preferably liquid and flowable, that also comprise waxes, medicaments, sealants, emulsions, abrasives, adhesives, friction reducers, encapsulated compositions, flavors, pharmaceutically active compositions, or any combination or mixtures thereof. The formulation contained within any second or additional container or reservoir is also a flowable formulation that is aerosolized upon application of force upon exiting the opening of a nozzle. More preferably, each second or additional formulation contained within each second or additional container or reservoir is a flowable, liquid formulation comprising a pharmaceutically active drug dissolved or dispersed in an excipient carrier effective in the treatment, amelioration or modification of gum, tooth or mouth disease. When the formulation or parts thereof must be stored in a dry state, the secondary or additional container further includes additional containers which hold liquid that can be combined with the dry drug of another container immediately prior to aerosolization.

The apparatus described herein is preferably a closed system. By the term "closed system" is meant that the apparatus or device of the invention described herein is encompassed by an outer surface so that the aerosolized formulation is essentially not in airborne communication with the atmosphere outside the apparatus. By "essentially" is meant that the closed system includes one or more openings through which a fiber can enter and/or exit during the coating process, however, such openings do not permit substantially measurable amounts of aerosol to escape the apparatus and enter the surrounding atmosphere. Such a closed system is advantageous by protecting employees who work in areas near the machinery used in coating the fibers described herein from contact with aerosolized particles.

Referring to the FIGURE, there is shown an exploded end view of a coating apparatus comprising a spray nozzle 1 that administers aerosolized coating formulation in the mist form on the floss fiber 2 that travels through the spray range 3 of the apparatus. There is a spray containment casing 4 that prevents aerosol spray from release into atmosphere. The casing 4 fits into grooves 5. The over spray that does not attach to the fiber 2 falls into an over spray receiving area 6, which is a flat plate heated by heater band 7. The heated collecting surface renders the over spray flowable and it is flowed into a container (not shown).

The floss is held taut and pulled through the spray range 3, and upon drying, is collected by spooling or other appropriate means. The overspray may be conveniently collected by disposing receiving area 6 is a slanted or vertical position so that the heated overspray flow is downwardly directed.

EXAMPLES

The following examples are intended to illustrate but not limit the invention. While they are typical of those that might be used, other procedures known to those skilled in the art may alternatively be used.

Example 1

Fiber Testing

Two methods of applying a coating formulation to a fiber were compared. One, the traditional "roller" method, involves dragging a fiber across a rotating surface covered in heated wax. The heated wax is delivered to the rotating surface by submerging a lower portion of a roller in a heated coating formulation. The coating is transferred to the floss as it contacts the formulation while moving across the roller. The second method, the method of the present invention, is the "aerosolized" method, by which a fiber coating formulation is aerosolized and the ejectile path of the resulting aerosolized particles intersect a target area of a fiber thereby coating and impregnating the fiber.

All testing reported herein was carried out comparing these two fiber coating methods to determine the efficacy of the "aerosol" method v. The "roller" method prior to its adoption for use in manufacturing oral hygiene products.

Typically when manufacturing coated fibers for oral hygiene products bulk fiber is supplied as a continuous single fiber wrapping a cylindrically shaped creel similar to the manner in which thread is stored on a bobbin as used in home sewing. The fiber is threaded through a winding machine onto an empty take-up creel that transfers the fiber from the latter to the former creel. As the fiber moves various coating formulations can be applied.

For the tests reported in the following examples, bobbin winding machines used in this manufacturing process were retrofitted with the enclosed containment apparatus of the invention similar to that shown in FIG. X. All tests reported herein, employed such an apparatus.

Example 2

Consistency of the Level Coating of the Fiber

To determine if the coating formulation maintained a consistent coating over the entire length of the treated fiber, tests were conducted measuring coating formulation levels at the beginning, middle, and end of the fiber. Additionally, the consistency of the level of coating was assessed comparing different nozzle pressures at the aperture.

A preliminary analysis was obtained by weighing fiber samples before and after the two treatments. The results indicated that aerosolization produced a degree of coating consistency comparable to the roller method. More comprehensive testing involved washing the treated fiber samples before weighing, since washing eliminated any coating formulation not adequately bound to the fiber. The results of these tests are presented in Table 1 and summarized in Table 2.

The results demonstrate that the coating level of aerosolized fibers of was consistent throughout the entire length of the fiber when the tests were compared using a bobbin associated with a particular nozzle and containment chamber. However, when comparing the consistency and degree of coating between different nozzles and containment chamber, the coating results were inconsistent.

TABLE 1

Aerosol Nozzle room temp
Pump 550 steps
20 PSI

| | Head I Coating % By Washing | | | Head II By Washing | | | Head III By Washing | | | Head IV By Washing | | |
|---|---|---|---|---|---|---|---|---|---|---|---|---|
| | 1 | 2 | Avg. | 1 | 2 | Avg. | 1 | 2 | Avg. | 1 | 2 | Avg. |
| 9:35 A.M. | | | | | | | | | | | | |
| Full | 44.6 | 46.7 | 45.7 | 63.1 | 60 | 61.55 | 62 | 59 | 60.5 | 63.4 | 59.8 | 61.6 |
| mid | 43.1 | 45.3 | 44.2 | 62.4 | 60 | 61.20 | 59.4 | 56.6 | 58 | 61.8 | 62.1 | 62 |
| End | 34.1 | 29.4 | 31.8 | 45.2 | 60.3 | 52.75 | 44.4 | 54.7 | 49.55 | 36 | 62.4 | 49.2 |
| Bobbin dia. | 28.7 | | | | 28.6 | | | 28.1 | | | 27.8 | |
| 11:15 A.M. | | | | | | | | | | | | |
| Full | 45.5 | 45.3 | 45.4 | 65 | 64 | 64.50 | 65.2 | 65.7 | 65.45 | 71.8 | 69.3 | 70.6 |
| mid | 44 | 39.6 | 41.8 | 63.2 | 61.2 | 62.20 | 62.4 | 60.2 | 61.3 | 69.5 | 68.7 | 69.1 |
| End | 32.8 | 34 | 33.4 | 55.8 | 63.3 | 59.55 | 38.6 | 37.5 | 38.05 | 37.7 | 62.5 | 50.1 |
| Bobbin dia. | 31.2 | | | | 28.6 | | | 28.8 | | | 28.2 | |

TABLE 2

Roller vs. Aerosolized Coating Consistency

| | Coating level | | Variation from first section | |
|---|---|---|---|---|
| Floss Section | Roller | Aerosol | Roller | Aerosol |
| 1 | 46.3 | 30.5 | 0.0 | 0.0 |
| 2 | 47.2 | 30.0 | 0.9 | -0.5 |
| 3 | 47.0 | 31.5 | 0.7 | 1.0 |
| 4 | 50.7 | 32.5 | 4.4 | 2.0 |
| 5 | 53.2 | 34.5 | 6.9 | 4.0 |
| 6 | 63.8 | 40.0 | 17.5 | 9.5 |
| 7 | 80.8 | 58.8 | 34.5 | 28.3 |
| 8 | 53.7 | 41.7 | 7.4 | 11.2 |

For example, the variation between nozzle 1 and 4 at 20 psi was 15.9%, between nozzle 2 and 3 at 50 psi the variation was 26.8%, and between nozzle 1 and 2 at 50 psi the variation was 27.9%. The inconsistent coating results using different nozzles indicated that standardization of the nozzle shape and pressure was required to optimize the aerosol method.

Example 3
Nozzle and Pressure Variation

Accordingly after the initial testing results of Example 2 were analyzed, various nozzle apertures and pressures were tested to determine the optimum shape and pressure range for aerosolization of the coating formulation. The results are presented in Table 3.

TABLE 3

| Sample AR 94N30 | Wt. of empty container | Wt. of floss Initial & Container | Wt. of floss initial | Wt. of floss final & container | Wt. of floss final | % Coating | Average |
|---|---|---|---|---|---|---|---|
| Hole #1 | | | | | | | |
| 600 (10 psi) | 1.562 | 2.1083 | 0.5463 | 1.9061 | 0.3441 | 58.76 | 59.11 |
| | 1.5624 | 2.1132 | 0.5508 | 1.9078 | 0.3454 | 59.47 | |
| 600 (5 psi) | 1.559 | 2.1161 | 0.5571 | 1.9121 | 0.3531 | 57.77 | 57.52 |
| | 1.5625 | 2.1073 | 0.5448 | 1.9089 | 0.3464 | 57.27 | |
| 800 (5 psi) | 1.5628 | 2.1086 | 0.5458 | 1.9093 | 0.3465 | 57.52 | 58.05 |
| | 1.5626 | 2.1246 | 0.562 | 1.917 | 0.3544 | 58.58 | |
| Hole #3 | | | | | | | |
| 600 (9 psi) | 1.5598 | 2.0205 | 0.4607 | 1.9752 | 0.4154 | 10.91 | 11.45 |

TABLE 3-continued

| Sample AR 94N30 | Wt. of empty container | Wt. of floss Initial & Container | Wt. of floss initial | Wt. of floss final & container | Wt. of floss final | % Coating | Average |
|---|---|---|---|---|---|---|---|
|  | 1.5656 | 2.0354 | 0.4698 | 1.9851 | 0.4195 | 11.99 |  |
| 600 (20 psi) | 1.5604 | 2.0303 | 0.4699 | 1.9024 | 0.342 | 37.40 | 37.23 |
|  | 1.5707 | 2.0477 | 0.477 | 1.9187 | 0.348 | 37.07 |  |
| Hole #4 |  |  |  |  |  |  |  |
| 600 (5 psi) | 1.5593 | 2.0383 | 0.479 | 1.938 | 0.3787 | 26.49 | 26.08 |
|  | 1.5604 | 2.0107 | 0.4503 | 1.9187 | 0.3583 | 25.68 |  |
| 600 (8 psi) | 1.5616 | 2.0087 | 0.4471 | 1.898 | 0.3344 | 33.70 | 33.27 |
|  | 1.5646 | 2.0281 | 0.4635 | 1.9135 | 0.3489 | 32.85 |  |
| 600 (10 psi) | 1.5623 | 2.0165 | 0.4542 | 1.907 | 0.3447 | 31.77 | 32.39 |
|  | 1.5675 | 2.0285 | 0.461 | 1.9141 | 0.3466 | 33.01 |  |

An analysis of the results indicate that a spherical nozzle aperture (i.e., hole #1) and a pressure in the range of about from 10 psi to about 25 psi produced the optimum fiber coating (measured as a percentage of the fiber coating).

Example 4
Fiber characteristics After Aerosolization

To determine if aerosolization altered normal fiber characteristics, fiber samples from the aerosol method were tested for: 1) tensile strength; 2) stretch and recovery; 3) separation (which indicates fiber wear); and 4) degree of fraying.

The results (not shown here) indicate that the fiber characteristics of aerosolized fibers are well within the specification goals that were found for roller treated fibers. Among aerosolized fibers, the mechanical strength of the fiber was maintained and both fiber separation and memory were normal. Therefore, it was concluded that aerosol treatment produced no greater fiber damage than roller treatment.

Example 5
Brush Diameter After Fiber Aerosolization

To determine if aerosolization diminished the brush diameter or baulk section of the fiber, two separate fiber trials were carried out comparing each coating method. The results are presented in Table 4. These results demonstrate that no significant detrimental effect on brush diameter was caused by aerosolization. Accordingly, these results also support the adoption of the aerosol method.

TABLE 4

| Aerosolized Treated Fiber | | | Untreated Fiber | | | Roller Treated Fiber | | |
|---|---|---|---|---|---|---|---|---|
| 1 Mm | 2 mm | Avg. mm | 1 mm | 2 mm | Avg. mm | 1 mm | 2 mm | Avg. mm |
| 1.67 | 1.31 | 1.59 | 1.28 | 1.67 | 1.37 | 1.52 | 1.58 | 1.49 |
| 1.65 | 1.43 | 1.54 | 1.86 | 1.20 | 1.53 | 1.61 | 1.38 | 1.49 |
| 2.01 | 1.20 | 1.61 | 1.72 | 1.30 | 1.51 | 1.86 | 1.31 | 1.58 |
| 1.71 | 1.32 | 1.55 | 1.37 | 1.69 | 1.53 | 1.76 | 1.28 | 1.52 |
| 1.36 | 1.67 | 1.50 | 1.68 | 1.32 | 1.79 | 1.52 | 1.86 | 1.6? |
| 1.22 | 1.58 | 1.41 | 1.98 | 1.21 | 1.58 | 1.51 | 1.76 | 1.63 |
| 1.69 | 1.27 | 1.45 | 1.43 | 1.72 | 1.57 | 1.76 | 1.33 | 1.54 |
| 1.56 | 1.38 | 1.56 | 1.62 | 1.32 | 1.57 | 1.82 | 1.57 | 1.69 |
| 1.58 | 1.53 | 1.50 | 1.71 | 1.23 | 1.57 | 1.26 | 1.55 | 1.?0 |
| 1.87 | 1.33 | 1.59 | 1.36 | 1.55 | 1.?5 | 1.31 | 1.61 | 1.56 |
|  | X = | 1.510 |  | X | 1.507 |  |  | 1.544 |

Example 6
Degree of Overspray During Aerosolization

To determine the amount of overspray created by the aerosol method, overspray trapped inside the containment apparatus, was collected and weighed after one round of fiber coating was completed. The weight of overspray collected was compared to the weight of the total material that was aerosolized during the test run. Using this technique, the average percentage of overspray was determined to be in the range of about 27.7% of the total coating formulation used.

Example 7
Comparative Chemical Analysis of the Original Coating Formulation to the Recaptured Overspray To determine if the overspray could be recycled and reused in subsequent coating applications, a chemical comparison of the coating formulation before aerosolization (designated the native formulation) and after aerosolization (designated the recaptured formulation) was conducted.

Samples (0.5 grams) of the native and recaptured overspray formulation were placed in a container with 10 ml of acetone. The container was agitated permitting the acetone to separate the volatile components of the formulation from the insoluble lipids. The mixture was subsequently cooled to solidify the wax separating it from the remaining composition. An aliquot of the supernatant from each sample was removed and injected under identical conditions into a mass spectrophotometer. The peak areas of 10 components of the coating formulation were then compared. The relative abundance of a component from the recaptured overspray sample was determined as a percentage of that same component compared to the native sample (which was assigned a value of 100%). The results are presented in Table 5 below.

TABLE 5

Recaptured Components as a Percentage of Native Coating Formulation

| Component | Native | Recaptured |
|---|---|---|
| Alpha Pinene | 100% | 71.75% |
| Limonene | 100% | 71.05% |
| Methone | 100% | 89.41% |
| Iso Methone | 100% | 85.94% |
| Menthyl Acetate | 100% | 93.56% |
| Menthol | 100% | 95.27% |
| Piperitone | 100% | 93.68% |
| L Carvone | 100% | 93.20% |
| Trans Anethole | 100% | 100% |
| Thymol | 100% | 93.30% |

To determine if one particular component of the formulation was preferentially affected during aerosolization recapture and recycle, the relative percentage of each component tested within the native and recaptured coating formulation was compared. These results are presented in Table 6.

TABLE 6

Percentage of Each Component of Native and Recaptured Coating Formulations

| Component | Native | Recaptured |
|---|---|---|
| Alpha pinene | 0.59 | 0.46 |
| Ethyl Iosvalerate | 0.08 | 0.07 |
| Beta Pinene | 0.17 | 0.14 |
| Alpha Sabine | 0.08 | 0.08 |
| Myrcene | 0.10 | 0.08 |
| Limonene | 1.08 | 0.82 |
| Cis Beta Ocimene | 0.00 | 0.01 |
| Trans Beta Ocimene | 0.03 | 0.03 |
| Para Cymene | 0.06 | 0.08 |
| 3-Octanol | 0.10 | 0.10 |
| Methone | 9.62 | 9.20 |
| Methone, Iso | 2.07 | 1.91 |
| C16-3-Hexenyl Isovalerate | 0.17 | 0.17 |
| Beta Elemene | 0.37 | 0.36 |
| Linolool | 0.15 | 0.17 |
| Menthyl Acetate | 2.24 | 2.23 |
| Iso Pulegol | 0.87 | 0.77 |
| Beta Caryophyllene | 1.35 | 1.31 |
| Neo Menthol | 1.94 | 2.06 |
| Menthol | 58.21 | 59.34 |
| Dihydrocarveyl Acetate | 0.79 | 0.74 |
| Germagrene D | 1.29 | 1.17 |
| Piperiton | 1.82 | 1.83 |
| L-Carvone | 12.32 | 12.28 |
| A Terpinyl Acetate Peak | 0.97 | 0.91 |
| Trans Anethole | 2.49 | 2.66 |
| Cis Carveol | 0.15 | 0.17 |
| Thymol | 0.90 | 0.91 |
| Total | 100.00 | 100.00 |

The results indicate that the recaptured overspray can successfully be reused in subsequent fiber coatings. The chemical loss of the recaptured formulation was 5.7% loss by weight which was calculated to be approximately one half the loss of formulation when employing the roller method.

Example 8

Consumer Evaluation Report

To determine whether consumers are likely to perceive differences between oral hygiene products made from fibers of the two methods, a panel of sensory experts was recruited to determine whether any difference in appearance, tactility, and flavor could be perceived between the two product types.

Tested characteristics were rated on a scale ranging from 0 to 15 (where 0=no perceived characteristic and 15=the strongest perceived characteristic). All fiber products compared were labeled with letter codes using a double-blind method. Subsequently, identification of the production method employed (i.e. "roller" v. "aerosol") was revealed after testing was completed.

The testing panel consisted of experts able to identify product attributes with a high degree of accuracy. Their assessment of the fiber types was assumed to be very conservative since their ability to identify product qualities is more acute than the average consumer. Therefore, it was hypothesized that if the two types of fiber products were not judged significantly different from each other then the average consumer would perceive no differences between the products.

The following terminology was used to describe the appearance of the treated fibers.

| | |
|---|---|
| Color Lightness | the intensity or strength of the lightness of the color. |
| Chroma | the brightness or purity of the color from dull/muddied to pure/bright. |
| Shininess | the amount of light reflected off the surface of the sample. |
| Pearlescence | the amount of pearly shine or gloss such as on the surface of Mother-of-pearl. |
| Width | the visual width of the floss across the flat surface. |
| Thickness | the visual thickness of the floss measured on the cross section. |
| Denseness | the degree of compactness of the fibers. |
| Distinctness of Fiber | the degree to which individual fibers are visible. |
| Evenness of Texture | the degree to which the texture of pattern of the fibers repeats itself along the sample. |
| Tensile Stretch | the degree to which the sample stretches from its original shape. |
| Shredding After Use | the degree to which the fibers separate from the sample after being pulled through the teeth. |

The following terminology was used to assess the manual tactility of the treated fibers.

| | |
|---|---|
| Stickiness | the degree to which the fingers stick to the sample when touched. |
| Roughness | the degree to which the sample feels irregular and rough as it is pulled gently through the thumb and index finger. |
| Slippery - dry & wet | the ease with which the sample glides through the thumb and index finger. |
| Pliable | the degree to which the sample folds and bends itself without sharp edges. |
| Wax Residue | the amount of waxy residue left on the fingers after sample manipulation. |

The following terminology was used to assess the oral tactility of the treated fibers.

| | |
|---|---|
| Force to slide between teeth | the force required to slide the sample between the teeth. |
| Sharpness against gums | the degree to which the sample feels sharp as it moves across the gum. |
| Ease to move in teeth crevices | the ease with which the sample can be moved back and forth through the crevices between the teeth. |
| Ease to pull out teeth. | the ease to pull the sample out from between the teeth. |
| Wax Residue | the amount of wax residue left on the teeth and gums from manipulation of the sample between the teeth. |

The following terminology was used to assess the flavor of the treated fibers.

| | |
|---|---|
| Mint | the aromatics associated with the overall impact of mint flavor. |
| Sweet | the taste on the tongue associated with sugars and artificial sweeteners. |
| Bitter | the taste on the tongue associated with caffeine and other bitter substances. |
| Cool | the cooling sensation in the mouth produced by substances such as menthol or mint. |
| Burn | the burning sensation in the mouth caused by certain substances which dehydrate the mouth such as strong solutions of vinegar, sucrose, salt, vodka, etc. |

The results of the consumer panel testing are presented in Table 7.

TABLE 7

SENSORY EVALUATION OF FIBERS

|  | Roller | Aerosol |
|---|---|---|
| APPEARANCE | | |
| Color Lightness | 8 | 8 |
| Color Chroma | 8 | 8 |
| Shininess | 2 | 2 |
| Pearlesence | 3 | 3 |
| Width | 10 | 9 |
| Thickness | 10 | 9 |
| Denseness | 4 | 4 |
| Distinctness of Fiber | 12 | 13.5 |
| Evenness of Texture | 10 | 8 |
| Tensile Stretch | 9 | 9 |
| Shredding after use | 2 | 0 |
| TACTILE FACTORS | | |
| MANUAL | | |
| Stickiness | 0 | 0 |
| Roughness | 7.5 | 6–9 variable |
| Slippery Dry | 5 | 4–6 |
| Slippery Wet | 9 | 10 |
| Pliable | 12 | 12 |
| Wax Residue | 2 waxy | 4.5 greasy/waxy |
| ORAL | | |
| Force to slide between teeth | 10 | 9 |
| Sharpness against gums | 6 | 5 |
| Ease to move in teeth crevice | 12 | 12 |
| Ease to pull out | 12 | 13 |
| Wax residue | 0 | 0 |
| FLAVOR | | |
| Mint | 3.5 | 7.0 |
| Sweet | 3 | 3 |
| Cool | 10 | 12 |
| Burn | 6 | 6 |
| Bitter | 3 | 3 |

The only significant difference judged between the roller or aerosolized fiber was in the category: "intensity of mint taste". The aerosolized fiber was judged to have a significantly more intense mint flavor than the flavor of the roller fiber. The aerosol fiber was perceived to be slightly more "greasy" and shredded less than the roller fiber. However, these differences were slight and not determined to be statistically significant or expected to be perceived by the 'average' consumer.

Overall, there very few differences were judged to exist between the two fibers and any perceived differences were judged too slight to be perceived by the average consumer. Although the invention has been described with reference to the presently preferred embodiment, it should be understood that various modifications can be made without departing from the spirit of the invention. Accordingly, the invention is limited only by the following claims.

What is claimed is:

1. A method of manufacturing a coated fiber for use in oral hygiene comprising: aerosolizing a coating formulation which includes a wax at ambient temperature; and delivering the aerosolized particles of the coating formulation onto a target area of a fiber.

2. The method of claim 1, wherein the fiber is a natural fiber, a synthetic fiber or combination thereof.

3. The method of claim 1, wherein the fiber traverses the path of aerosolized particles of the coating formulation.

4. The method of claim 1, wherein the coating formulation is further comprised of at least one of a wax, a medicament, a sealant, an emulsion, an abrasive, an adhesive, a friction reducer, an encapsulated composition, a flavor or any combination thereof.

5. The method of claim 4, wherein said formulation further contains a volatile compound.

6. The method of claim 5, wherein the volatile compound includes the flavor.

7. The method of claim 5, wherein the volatile compound includes the medicament.

8. The method of claim 7, wherein the medicament includes an anti-carries agent, or fluorides, or the encapsulated composition.

9. The method of claim 1, wherein the step of aerosolization is performed by means of force caused by pressure, electrical field, electromagnetism or gravity.

10. A method for delivering an aerosolized volume of a coating in a target area of a fiber used in oral hygiene comprising:

drawing air under force into a dispensing apparatus containing a coating formulation;

applying force to the air and to the coating formulation comprised of wax and an additive, sufficient to drive the coating formulation through an aperture of a nozzle to create an aerosolized volume of coating formulation whose ejectile path from the nozzle intersects a target area of a moving fiber;

recovering coating formulation not deposited on the target area of the moving fiber that is deposited on a surface behind the target area of the moving fiber by heating the surface sufficiently to cause any deposited coating formulation to flow.

11. The method according to claim 10 further comprising the step of returning the recovered coating formulation to the dispensing apparatus.

* * * * *